United States Patent
Carlson et al.

(10) Patent No.: US 6,572,896 B1
(45) Date of Patent: Jun. 3, 2003

(54) METHODS FOR INHIBITING CELL MOTILITY

(75) Inventors: C. George Carlson, R.R.#1, Box 220, Kirksville, MO (US) 63501; James L. Cox, R.R.#3, Box 82B, Kirksville, MO (US) 63501

(73) Assignees: A.T. Still University of Health Sciences, Kirksville, MO (US); C. George Carlson, Kirksville, MO (US); James L. Cox, Kirksville, MO (US)

( * ) Notice: Subject to any disclaimer, the term of this patent is extended or adjusted under 35 U.S.C. 154(b) by 0 days.

(21) Appl. No.: 10/156,985

(22) Filed: May 28, 2002

Related U.S. Application Data

(63) Continuation of application No. 09/668,233, filed on Sep. 22, 2000, now abandoned, which is a continuation-in-part of application No. 09/016,196, filed on Jan. 30, 1998, now abandoned.

(51) Int. Cl.$^7$ .................. A61K 33/24; C12N 5/00; C12Q 1/02
(52) U.S. Cl. ................ 424/617; 435/29; 435/325; 435/375
(58) Field of Search ................ 424/617, 722; 435/29, 325, 375

(56) References Cited

U.S. PATENT DOCUMENTS 5,759,855 A * 6/1998 Pierschbacher et al. ..... 435/325

FOREIGN PATENT DOCUMENTS

| JP | 64-90127 | * | 4/1989 |
| WO | 90/025556 | * | 3/1990 |

OTHER PUBLICATIONS

WEST online, file DWPI, Acc. No. 1997–259630 (Li, CN 1100951 (1995)), Abstract.*
Albelda et al., "Integrin Distribution in Malignant Melanoma:Association of the [Beta sub–3] Subunit with Tumor Progression" Cancer Research, vol. 50, pp. 6757–6764.*
Meyer et al., "Mechanisims of Tumour Metastasis" European Journal of Cancer, vol. 34, pp. 214–221.*
Gailit et al., "Regulation of the Fibronectin Receptor Affinity by Divalent Cations" Journal of Biological Chemistry, vol. 263, No. 26, pp. 12927–12932.*

* cited by examiner

Primary Examiner—Jose' G. Dees
Assistant Examiner—Frank Choi
(74) Attorney, Agent, or Firm—Hovey Williams LLP

(57) ABSTRACT

A method is provided for inhibiting and substantially decreasing the motility of cells, and especially melanoma cells. In the invention, a cell is contacted with a motility-inhibiting amount of a metal ion selected from the group consisting of cobalt ion, the lanthanide metal ions, and mixtures thereof; particularly preferred metal ions are the $Co^{2+}$ and $Gd^{3+}$ ions. Metal ion sources may be administered in the form of soluble metal halide salts to in vitro to cells dispersed in an aqueous saline medium, or by administering an aqueous dispersion thereof to an in vivo mammalian subject at or adjacent a tumor site.

14 Claims, No Drawings

METHODS FOR INHIBITING CELL MOTILITY

RELATED APPLICATIONS

This application is a continuation application of U.S. patent application Ser. No. 09/668,233, filed Sep. 22, 2000, now abandoned, and incorporated by reference herein. U.S. patent application Ser. No. 09/668,233 is a continuation-in-part application of U.S. patent application Ser. No. 09/016,196, filed Jan. 30, 1998, now abandoned and incorporated by reference herein.

BACKGROUND OF THE INVENTION

1. Field of the Invention

The present invention is concerned with methods for inhibiting and decreasing cell motility (and particularly that of melanoma cells) by contacting such cells with relatively minor amounts of metal ion(s) selected from the group consisting of cobalt ion, the lanthanide metal ions, and mixtures thereof. In practice, metal ion sources (e.g., the metal halide salts) are solubilized in an aqueous medium and are administered to melanoma cells to achieve motility inhibition.

2. Description of the Prior Art

Metastasis, the spread of cancerous cells from an initial tumor to other physically separate sites in the body, is a common and life-threatening situation in many cancers. Although the precise mechanism of metastasis is not known, directional migration of melanoma cells in response to concentration gradients of soluble factors (chemotaxis) and overall motility of melanoma cells is clearly an important factor.

Savarese et al., Type IV Collagen Stimulates and Increase in Intracellular Calcium; Potential Role in Tumor Cell Motility; *J Biol. Chem.*, 267(30):21928–21935 (1992) examined the influence of two metal ions ($Co^{2+}$ and $La^{3+}$) on motility of A2058 human melanoma cells. The concentration of $Co^{2+}$ used in this study ($10^{-8}$ to $10^{-4}$ M) was completely ineffective to inhibit tumor cell motility. Indeed, only one of six agents (nifedipine) at a concentration of 100 $\mu$M was reported to produce inhibition of motility.

$Co^{2+}$ is widely known and used for its effects in blocking $Ca^{2+}$ currents in a variety of cell systems. The concentration of $Co^{2+}$ utilized is based on 1979 experiments in which $CoCl_2$ was used to block neuromuscular transmission. $Gd^{3+}$ is also known as a highly potent channel blocking agent for stretch-sensitive non-selective cation channels, and may be more selective for this channel type as compared with voltage-gated $Ca^{2+}$ channels. For example, a recent study indicates that $Gd^{3+}$ (up to 100 $\mu$M), in contrast to $Co^{2+}$ has no effect on the voltage-gated channels that control quantal neurotransmitter release at the mammalian neuromuscular junction (Porter et al., *Br. J Pharmacol.*, 118:27–32 (1996)). Additional reports indicate an effect of $Gd^{3+}$ on voltage-gated $Ca^{2+}$ channels in isolated guinea pig ventricular myocytes (Lacampagne et al.; *Biochem. Biophys. Acta.*, 1191:205–208 (1994)) and cultured pituitary cells (Biagi et al., *Amer. J. Physiol.*, 259:C515–C520 (1990)). At present, the primary medical use for gadolinium involves chelated forms of the element used as contrast agents in magnetic resonance imaging. However, there are no previous reports on the use of gadolinium ion for decreasing melanoma cell motility.

U.S. Pat. No. 4,690,935 deals with selective blockers of voltage-gated $Ca^{2+}$ channels in tumor cell metastasis. U.S. Pat. No. 5,045,543 describes 5-amino or substituted amino 1,2,3-triazoles as being effective against progressive metastatic cancers (Kohn et al, *Cancer Res.*, 56:569–573 (1996)). These patents do not disclose the utility of cobalt or the lanthanide metal ions for inhibiting melanoma cell motility.

SUMMARY OF THE INVENTION

The present invention describes a novel method for inhibiting cell motility comprising the step of contacting a cell with a motility-inhibiting amount of a metal ion selected from the group consisting of cobalt ion, the lanthanide metal ions (La, Ce, Pr, Nd, Pb, Sm, Eu, Gd, Tb, Dy, Ho, Er, Tm, Yb and Lu). Through use of the present invention, a decrease in motility of at least about 50%, and more preferably from about 70–95%, can be obtained, as compared with the motility of the cell under identical conditions, but in the absence of the metal ion contacting step.

In more detail, the contacting step is preferably carried out by administering a metal ion source for cell contact by dispersing the metal ion source in an aqueous saline system having a motility-inhibiting metal ion concentration of from about 20 $\mu$M to about 2 mM. The preferred metal ion sources are the corresponding metal salts, and particularly the halogen salts such as the chloride salts.

The most preferred metal ions for use in the invention are selected from the group consisting of cobalt and gadolinium ions and mixtures thereof. Where gadolinium ion is employed, the ion concentration of the liquid system used for motility inhibition should be from about 1–200 $\mu$M, preferably from about 10–100 $\mu$M, more preferably from about 20–50 $\mu$M, and even more preferably about 20 $\mu$M. Correspondingly, where cobalt ion is employed, the ion concentration of the liquid system is most preferably about 2 mM.

The contacting step of the invention may be carried out in vitro and in such instances the cell is dispersed in a liquid saline cell-supporting medium, and selected motility-inhibiting metal ions are added to the medium to achieve the desired ion concentration. Preferably, the medium should be maintained at a temperature of from about 30–44° C. and the contacting step is carried out under a $CO_2$-enriched atmosphere (e.g., 5% by volume $CO_2$). In such instances, additional cell motility inhibition can be obtained by adjusting the potassium ion concentration of the cell-supporting liquid medium, preferably to a level of below about 0.5 mM or above about 30 mM. The invention can also be carried out in vivo by administration of metal ion (typically a halogen salt thereof dispersed in a liquid saline carrier) to a mammalian subject at or near the site of a potentially metastatic tumor.

DETAILED DESCRIPTION OF THE PREFERRED EMBODIMENTS

The following examples set forth studies demonstrating the utility of metal ions in accordance with the invention, in the context of significantly inhibiting the motility of melanoma cells. It is to be understood however that these examples are provided by way of illustration only, and nothing therein should be taken as a limitation upon the overall scope of the invention.

MATERIALS AND METHODS

B16F10 melanoma cells were obtained from the M. D. Anderson Cancer Center, Houston, Tex. Cells were cultured in 5% fetal calf serum in RPMI media supplemented with antibiotics. Growth of the cells was in 5% $CO_2$ at 37° C. until subconfluence was reached.

The compositions of the various solutions used in the tests were as follows:

RPMI-1640 solution—available from Sigma Chemical Company;

RPMI-E solution—0.42 mM $Ca(NO_3)_2$, 0.4 mM $MgSO_4$, 5.4 mM KCl, 23.8 mM $NaHCO_3$, 108.6 mM NaCl, 5.0 mM HEPES, 11.1 mM glucose, and a pH of 7.3. This is the glucose and electrolyte composition of the RPMI—1640 Media;

RPMI-E2 solution—0.42 mM $CaCl_2$, 0.4 mM $MgCl_2$, 5.4 mM KCl, 132.0 mM NaCl, 5.0 mM HEPES, 11.1 mM glucose, and a pH of 7.3;

RPMI-E2 low $K^+$ solution—0.42 mM $CaCl_2$, 0.4 mM $MgCl_2$, 0.54 mM KCl, 136.86 mM NaCl, 5.0 mM HEPES, 11.1 mM glucose, and a pH of 7.3;

RPMI-E2 high $K^+$ solution—0.42 mM $CaCl_2$, 0.4 mM $MgCl_2$, 54 mM KCl, 83.4 NaCl, 5.0 mM HEPES, 11.1 mM glucose, and a pH of 7.3;

RPMI-E4Ca solution—0.42 mM $Ca(NO_3)_2$, 0.4 mM $MgSO_4$, 5.4 mM KCl, 23.8 mM $NaHCO_3$, 103.2 mM NaCl, 3.6 mM $CaCl_2$, 5 mM HEPES, 11.1 mM glucose, and a pH of 7.3; and, High $Ca^{2+}$ HEPES Ringer Solution—5.0 mM KCl, 2.6 mM NaCl, 100 mM $CaCl_2$, 11.0 mM glucose, and a pH of 7.35.

Procedure Followed in Motility Assays

Subconfluent B16F10 cells were removed from dishes with a trypsin treatment (0.25%) for 5 minutes followed by two washings in RPMI-E2 solution. The cells were pelleted at 8000 g for 2 minutes, resuspended in the same solution, and counted with a hemocytometer. After adding 3 to $5 \times 10^4$ suspended cells to an Eppendorf tube, the cells were pelleted at 4000 g and resuspended in the experimental solution used for that particular assay with or without 20 $\mu$M $GdCl_3$ and/or 2 mM $CoCl_2$ as required by the particular assay.

The suspended cells for each test were then placed in the wells of blind-well migration chambers over which a gelatin coated (0.1% gelatin for 2 hours and then air-dried in laminar flow hood) filter was placed. The chamber was inverted and placed in a 37° C. (5% $CO_2$) atmosphere for 2 hours to allow the attachment of the cells to the gelatin-coated filter. The chamber was inverted once more, and the same suspension composition used for each test was placed in the upper compartment of the respective chamber. If Basic fibroblast growth factor (bFGF) was used in an experiment to enhance motility, then it was also added to the solution in the upper compartment at a concentration of 25 ng/ml.

Cell migration was allowed to occur for 5 hours at 37° C. (5% $CO_2$) in a humidified incubator. At the end of this period, the cells were permeabilized in 0.5% Triton X-100 for 1 minute followed by hematoxylin staining. The cells that had migrated to the top surface of the filters were counted using an Olympus (IMT-2) light microscope (400×). Alterations in motility were defined by changes in the number of cells that migrated to the top of the filter over the 5 hour incubation period.

Procedure Followed for Microscopic Examination of Cells

Cell morphology was examined under conditions that were used in the motility assays. B16F10 melanoma cells were cultured directly on gelatin coated glass cover slips (0.1% gelatin for 2 hours and then air dried) for 24 hours under standard cell culture conditions. Culture media was then removed and the cells were washed twice with phosphate buffered saline (PBS) before being exposed to either 0.54 mM, 5.4 mM, or 54 mM $K^+$ in iso-osmotic saline solutions that were based on the electrolyte composition of RPMI-1640 media. Some solutions also contained $GdCl_3$ or $TbCl_3$ in a concentration of 20 $\mu$M. The cells were incubated at 5% $CO_2$ and 37° C. for 4 hours before cells were photographed using an Olympus (IMT-2) inverted microscope.

EFFECT OF EXTRACELLULAR $Ca^{2+}$ CONCENTRATION ON THE MOTILITY OF B16F10 CELLS

In this control test, B16F10 cells were allowed to migrate in solutions that included only the electrolyte composition of RPMI-1640 media with 11.0 mM glucose. This migration took place under conditions of both normal (0.4 mM RPMI-E) and elevated (4 mM RPMI-E4Ca) extracellular calcium concentrations. As demonstrated by the data represented in Table 1, the elevated $Ca^{2+}$ produced about a 20% increase in the motility of the cells.

TABLE 1

Motility at Varied Concentrations of Extra cellular $Ca^{2+}$

| $Ca^{2+}$ Concentration (mM) | Motility[a] |
|---|---|
| 0.4 | 78 ± 4[b] |
| 4.0 | 100 ± 6 |

[a] mean number of cells per filter
[b] ± SEM; n = 4 filters per group; $p < 0.05$

STIMULATION OF CELL MOTILITY

In a second control, the assays were improved by using bFGF to increase motile cell numbers. bFGF produced a three-fold increase in the motility of melanoma cells when it was included (25 ng/ml in serum free RPMI-1640 media) in the top well of the motility chamber. This data is presented in Table 2. In all subsequent motility assays, bFGF was included at this concentration in both the control and experimental samples.

TABLE 2

Effect of bFGF on B16F10 Cell Motility

| Sample | Motility[a] |
|---|---|
| control (no bFGF) | 53 ± 2[b] |
| with bFGF | 180 ± 30 |

[a] mean number of cells per filter
[b] ± SEM; n = 4 filters per group; $p < 0.01$ EFFECT OF $Ca^{2+}$ BLOCKING AGENTS ON CELL MOTILITY

EXAMPLE 1

Metal—$Gd^{3+}$

The B16F10 cells were placed in an elevated $Ca^{2+}$ HEPES buffered solution (High $Ca^{2+}$ HEPES Ringer solution). The cells (2 to $5 \times 10^4$/well) were then exposed to $GdCl_3$ by addition thereof to the buffered solution at a concentration of 20 $\mu$M, for the two hour preincubation attachment period (37° C.), and for the five hour motility assay. The $Gd^{3+}$ significantly inhibited cell motility by 71%. The results are shown in Table 3.

EXAMPLE 2

Metal—$Co^{2+}$

The B16F10 cells were placed in an elevated $Ca^{2+}$ HEPES buffered solution (High Ca2+ HEPES Ringer solution). The cells (2 to $5×10^4$/well) were then exposed to $CoCl_2$ by addition thereof to the buffered solution at a concentration of 2 mM for the two hour preincubation attachment period (37° C.), and for the five hour motility assay. The $Co^{2+}$ significantly inhibited the motility by approximately 87%. The results are shown in Table 3.

EXAMPLE 3

Metal—$Gd^{3+}$+$Co^{2+}$

The B16F10 cells were placed in an elevated $Ca^{2+}$ HEPES buffered solution (High Ca2+ HEPES Ringer solution). The cells (2 to $5×10^4$/well) were then exposed to $GdCl_3$ plus $CoCl_2$ at a concentration of 20 $\mu$M $GdCl_3$ and 2 mM $CoCl_2$ by addition of these metal salts to the buffered solution, for the two hour preincubation attachment period (37° C.), and for the five hour motility assay. The two metals combined resulted in nearly complete inhibition of the motility, decreasing it by 95%. The results are shown in Table 3.

TABLE 3

Effect of $Ca^{2+}$ Channel Blockers on B16F10
Cell Motility at Elevated $Ca^{2+}$ Concentrations

| Metal Concentration | Motility[a] |
| --- | --- |
| Control (no metal)[b] | 326 ± 25[c] |
| $GdCl_3$ (20 $\mu$M) | 95 ± 6 |
| $CoCl_3$ (2 mM) | 43 ± 4 |
| $GdCl_3$ (20 $\mu$M) + $CoCl_2$ (2 mM) | 17 ± 2 |

[a]mean number of cells per filter
[b]control cells were placed in an elevated $Ca^{2+}$ HEPES buffered solution (High $Ca^{2+}$ HEPES Ringer solution). No metal was used in the control test.
[c]± SEM; n = 4 filters per group; p < 0.05

EXAMPLE 4

In two independent test runs, the B16F10 cells were exposed to $GdCl_3$ at concentrations of 20 $\mu$M in the RPMI-E2 solution with normal concentrations of $K^+$ and $Ca^{2+}$. In each run, the cells were exposed to the $GdCl_3$ for seven hours resulting in significant motility inhibition as shown in Table 4. The reduction was by 73% and 75% respectively.

TABLE 4

Effect of $Ca^{2+}$ Channel Blockers on B16F10
Cell Motility at Normal $Ca^{2+}$ Concentrations

| Metal Concentration (mM) | Motility[a] |
| --- | --- |
| Control (no $GdCl_3$)[b] | 121 ± 15[c] |
| $GdCl_3$ (20 $\mu$M) | 33 ± 6 |
| Control (no $GdCl_3$)[b] | 200 ± 13 |
| $GdCl_3$ (20 $\mu$M) | 50 ± 10 |

[a]mean number of cells per filter
[b]control cells were placed in the RPMI-E2 solution with normal concentrations of $K^+$ and $Ca^{2+}$. No metal was used in the control test.
[c]± SEM; n = 4 filters per group; p < 0.01

TOXICITY OF $Gd^{3+}$ ON B16F10 CELLS

EXAMPLE 5

Cell Viability

A test was run to determine the toxicity of $Gd^{3+}$ on cells when exposed for seven hours. B16F10 cells were incubated for 12 hours with $Gd^{3+}$ at a concentration of 20 $\mu$M in the RPMI-E2 solution. A different batch of B16F10 cells were incubated for 12 hours without $Gd^{3+}$ in the RPMI-E2 solution. The cells were then examined with a Trypan blue exclusion assay. There was no difference in viability between the cells which were treated with $Gd^{3+}$ and the cells which were not treated with $Gd^{3+}$. Less than 1% of the cells in either group stained blue.

EXAMPLE 6

Cell Growth

The potential long term effects of $Gd^{3+}$ on cell growth were determined. The B16F10 cells were incubated for 12 hours with $Gd^{3+}$ at a concentration of 20 $\mu$M in the RPMI-E2 solutions. The cells were then washed twice with PBS and supplemented with a growth medium (RPMI-1640 plus serum) which did not contain $Gd^{3+}$. The cell growth was observed after the $Gd^{3+}$ was washed from the cells. No obvious inhibitory effect on cell growth was observed in these cells when compared to cells which were never treated with $Gd^{3+}$.

MODIFICATION OF EXTRACELLULAR $K^+$

EXAMPLE 7

In order to determine whether resting $Ca^{2+}$ influx mediates melanoma cell motility, the electrochemical driving force for $Ca^{2+}$ influx was altered by modifying the extracellular $K^+$ concentration. Non-inactivating $K^+$ channels that modulate the cells resting potential and direct electrophysiological control of the membrane potential of cells produces steady state alterations in intracellular $Ca^{2+}$ that are consistent with predicted alterations in the resting rate of $Ca^{2+}$ influx secondary to changes in the driving force. Therefore, if resting $Ca^{2+}$ influx modulates the motility of melanoma cells, it would be expected that motility would be enhanced by reductions in the extracellular $K^+$ concentration because such reductions would make the membrane potential more negative and thus increase the electrochemical driving force which promotes $Ca^{2+}$ influx.

Table 5 shows the motility of B16F10 cells over a varying range of extracellular $K^+$. To achieve the $K^+$ concentrations shown in Table 5, three of the experimental solutions were varied in the following manner:

To achieve a $K^+$ concentration of 0.54 mM, only the RPMI-E2 low $K^+$ solution was used. The RPMI-E2 low $K^+$ solution and the RPMI-E2 solution were mixed together to achieve the $K^+$ concentrations of 2.75 mM and 3.87 mM. Only the RPMI-E2 solution was used to obtain a concentration of 5.4 mM.

To increase the $K^+$ above 5.4 mM, RPMI-E2 high $K^+$ solution was added to the RPMI-E2 $K^+$ solution.

To achieve the highest concentration of $K^+$—54 mM—only the RPMI-E2 high $K^+$ solution was used.

There is a substantial enhancement of motility when the $K^+$ is about 0.5 mM and when the $K^+$ is increased to above 30 mM. In between these two concentrations, the motility remained substantially constant.

TABLE 5

B16F10 Cell Motility at Varied K+ Concentrations and in the Absence of $Gd^{3-}$

| K+ Concentration (mM) | Motility[a] |
| --- | --- |
| 0.54 | 1387 ± 103[b] |
| 2.75 | 1164 ± 1006 |
| 3.87 | 591 ± 40 |
| 5.4 | 475 ± 20 |
| 10.0 | 578 ± 15 |
| 16.25 | 494 ± 49 |
| 22.0 | 558 ± 25 |
| 27.5 | 471 ± 57 |
| 35.0 | 646 ± 65 |
| 54.0 | 1188 ± 50 |

[a] mean number of cells per filter
[b] ± SEM; n = 4 filters per group

EXAMPLE 8

To determine whether the K+ dependent increases in motility were associated with effects secondary to resting $Ca^{2+}$ influx, the influence of $Gd^{3+}$ (at a concentration of 20 μM concentration) on motility was examined at both reduced (RPMI-E2 low K+ solution) and elevated (RPMI-E2 high K+ solution) K+ concentrations. Table 6 shows these results. The data shows that under conditions of enhanced motility, the blocking effect of $Gd^{3+}$ (which inhibited cell motility by 71% at normal K+ concentrations as shown in Example 1) was increased to values of 83% and 90.5% inhibition of cell motility at 0.54 and 54 mM K+ respectively. These results indicate that resting $Ca^{2+}$ influx contributes to the enhanced motility observed at both reduced and elevated K+ concentrations.

TABLE 6

Effect of $Gd^{3-}$ (20 μM) Channel Blockers on B16F10 Cell Motility at Varied K+ concentrations

| K+ Concentration (mM) | Control Motility[a] | Motility[a] |
| --- | --- | --- |
| 0.54 | 1387 ± 103 | 240 ± 40[b] |
| 54.0 | 1188 ± 50 | 113 ± 10 |

[a] mean number of cells per filter
[b] ± SEM; n = 4 filters per group

EFFECTS ON CELL MORPHOLOGY

EXAMPLE 9

In order to examine the effects of $Gd^{3+}$ and extracellular K+ concentration on the morphology of the cells, B16F10 melanoma cells were grown under normal conditions on gelatin-coated glass coverslips. The cells were then washed twice with PBS and placed in solutions containing the following concentrations of K+ and $Gd^{3+}$ for exposure periods of 4 hours:

(1) 0.54 mM K+ (RPMI-E2 low K+ solution) and 20 μM $Gd^{3+}$;
(2) 0.54 mM K+ (RPMI-E2 low K+ solution) and no $Gd^{3+}$;
(3) 5.4 mM K+ (RPMI-E2) and 20 μM $Gd^{3+}$ or 20 μM $Tb^{3+}$;
(4) 5.4 mM K+ (RPMI-E2) and no $Gd^{3+}$ or no $Tb^{3+}$;
(5) 54 mM K+ (RPMI-E2 high K+ solution) and 20 μM $Gd^{3+}$; and,
(6) 54 mM K+ (RPMI-E2 high K+ solution) and no $Gd^{3+}$.

At normal K+ concentrations (5.4 mM K+ and no $Gd^{3+}$ and no $Tb^{3+}$), the majority of the cells appeared spindle-shaped with filopodial processes. At low K+ concentrations (0.54 mM K+ and no $Gd^{3+}$), slightly more cells were observed with distinct lamellipodia. In contrast, cells at high K+ concentrations (54 mM K+ and no $Gd^{3+}$) were rounder and exhibited pseudopodia that appeared blunted in comparison with the cells bathed in normal K+ concentrations (5.4 mM K+).

When the bathing solution included 20 μM $Gd^{3+}$ or 20 μM $Tb^{3+}$, the cells had flattened and spread further indicating that the $Gd^{3+}$ lowered the motility of the cells. At normal concentrations of K+ and 20 μM $Gd^{3+}$, larger, rounded cells devoid of pseudopodia were observed. The solution containing low K+ and 20 μM $Gd^{3+}$ produced rounded and flattened cells with prominent vacuoles suggesting a loss of cell membrane integrity. However, subsequent exposure to Trypan Blue indicated that the vacuolated cells excluded dye, thereby indicating morphologically intact plasma membranes.

EFFECTS OF CONVENTIONAL VOLTAGE-GATED $Ca^{2+}$ CHANNEL ANTAGONISTS ON MOTILITY

The $Ca^{2+}$ channel antagonist verapamil was tested to determine its effect on motility. Verapamil was used at a concentration of 100 μM under control conditions (RPMI-E2 solution), high K+ conditions (RPMI-E2 high K+ solutions), and low K+ conditions (RPMI-E2 low K+ solutions). The results, shown in Table 7, show that verapamil treatment did not reduce motility in a way corresponding to the reduction produced by $Gd^{3+}$ and $Co^{2+}$. These results indicate that the antimotility effects of $Gd^{3+}$ and other blockers of resting $Ca^{2+}$ influx pathways are distinct from the relatively small effects of voltage-gated $Ca^{2+}$ channel antagonists on tumor cell metastasis.

TABLE 7

Effect of Verapamil (100 μM) on B16F10 Cell Motility

| K+ Concentration (mM) | Control Motility[a] | Motility with Verapamil[a] |
| --- | --- | --- |
| 5 mM K+ | 570[b] | 434[b] |
| 0.5 mM K+ | 1254 | 1116 |
| 5 mM K+ | 500 | 519 |
| 50 mM K+ | 1270 | 1100 |

[a] mean number of cells per filter
[b] n = 2 filters per group

We claim:

1. A method of inhibiting cell motility comprising the step of contacting a colony of cells dispersed in a liquid cell-supporting medium with a gadolinium ion, said contacting step comprising the step of adding a gadolinium ion source to said medium to achieve a gadolinium ion concentration of from about 10–100 μM.

2. The method of claim 1, including the step of maintaining said liquid medium at a temperature of from about 30–44° C. during said contacting step.

3. The method of claim 1, including the step of carrying out said contacting step in a 5% by volume $CO_2$ atmosphere.

4. The method of claim 1, said contacting step being carried out so as to decrease the motility of said colony of cells by a factor of at least about 50%, as compared with the motility of said colony of cells in the absence of said contacting step.

5. The method of claim 4, said motility decrease being from about 70–95%.

6. The method of claim 1, said cells being metastatic cells.

7. The method of claim 6, said cells being melanoma cells.

8. The method of claim 1, including the step of contacting said cells with a metal ion source selected from the group consisting of the halogen salts of the lanthanide metals.

9. The method of claim 8, said halogen salts being the chloride salts.

10. The method of claim 1, said contacting step being carried out for a period of at least about 1 hour.

11. The method of claim 10, said period being from about 2–7 hours.

12. The method of claim 1, said cells remaining viable after said contacting step.

13. A method of inhibiting cell motility comprising the step of contacting a colony of cells dispersed in a liquid cell-supporting medium with a gadolinium ion, said contacting step comprising the step of adding a gadolinium ion source to said medium to achieve a gadolinium ion concentration from about 20–50 $\mu$M.

14. A method of inhibiting cell motility comprising the step of contacting a cell dispersed in a liquid cell-supporting medium with gadolinium ions, said medium comprising a gadolinium ion concentration of about 20 $\mu$M.

* * * * *